United States Patent [19]

Reimer et al.

[11] 4,416,824

[45] Nov. 22, 1983

[54] RECOVERY OF TRIARYLBORANES BY FORMING BORON-CONTAINING METAL COMPOUNDS

[75] Inventors: Ronald A. Reimer; Gerald T. Stowe, both of Orange, Tex.

[73] Assignee: E. I. Du Pont de Nemours & Co., Wilmington, Del.

[21] Appl. No.: 333,176

[22] Filed: Dec. 21, 1981

[51] Int. Cl.$^3$ .................... C07F 15/00; C07F 15/04
[52] U.S. Cl. .................... 260/439 R; 260/464; 260/429 R; 260/438.1; 568/1
[58] Field of Search ............ 260/438.1, 439 R, 429 R, 260/464; 568/1

[56] References Cited

U.S. PATENT DOCUMENTS

| | | | |
|---|---|---|---|
| 3,644,453 | 2/1972 | Onsager | 260/439 R |
| 3,644,454 | 2/1972 | Onsager | 260/439 R |
| 3,676,481 | 7/1972 | Chia | 260/439 R X |
| 3,766,231 | 10/1973 | Gosser et al. | 260/439 R |
| 3,773,809 | 11/1973 | Walter | 260/465.8 R |
| 3,847,959 | 11/1974 | Shook, Jr. et al. | 260/439 R |
| 3,903,120 | 9/1975 | Shook, Jr. et al. | 260/439 |
| 4,046,815 | 9/1977 | Nazarenko | 568/1 X |
| 4,076,756 | 2/1978 | Nazarenko et al. | 568/1 |
| 4,082,811 | 4/1978 | Shook, Jr. | 568/1 |
| 4,134,923 | 1/1979 | Reimer | 568/1 |
| 4,251,468 | 2/1981 | Nazarenko | 568/1 |

FOREIGN PATENT DOCUMENTS 2047680A 12/1980 United Kingdom .

OTHER PUBLICATIONS

G. Wittig et al., Analytical Chemistry 573, 195 (1951).
R. J. Haines et al., Journal of Organometallic Chemistry, 84, 357 (1975).
M. Laing et al., Journal of Organometallic Chemistry, 82, C 40–42, (1974).
F. A. Cotton et al., Advanced Inorganic Chemistry, 4 Ed., p. 142, John Wiley & Sons, (1980).
D. L. Greene et al., Journal of Inorganic and Nuclear Chemistry, 35, 1471, (1973).

*Primary Examiner*—Helen M. S. Sneed

[57] ABSTRACT

A process for recovery of normally soluble triarylboranes in organonitriles by forming novel boron containing metal compounds, e.g., bis(triphenylborane-isocyano-N)-bis(adiponitrile)nickel (II).

11 Claims, No Drawings

RECOVERY OF TRIARYLBORANES BY FORMING BORON-CONTAINING METAL COMPOUNDS

BACKGROUND OF THE INVENTION

1. Field of the Invention

The present invention relates to the recovery of triarylboranes from solution in organonitriles by forming novel boron containing metal compounds and thereafter separating the metal compounds from the organic nitrile. Bis(triphenylboraneisocyano-N)-bis(adiponitrile)nickel (II) is illustrative of the metal compounds.

2. Description of the Prior Art

Numerous boron containing cyanide complexes have been described. A compound postulated to be the sodium cyanide adduct of triphenylborane having the formula $[\phi_3(NC)B]Na$ was reported by G. Wittig et al [Ann. Chem. 573, 195 (1951)]. The synthesis of Ru(-$\eta$—$C_5H_5$) $(CO)_2NCB\phi_3$ and its thermal rearrangement to Ru($\eta$—$C_5H_5$) $(CO)_2CN$ and Ru($\eta$—$C_5H_5$) $(CO)_2CNB\phi_3$ are reported by R. J. Haines et al, Journal of Organometallic Chemistry, 84, 357 (1975). A compound having Fe-C-N-$B\phi_3$ bonding is reported by M. Laing et al Journal of Organometallic Chemistry, 82, C 40–42 (1974).

A general discussion of nitrile functions and their ability to bond to metals is found in "Advanced Inorganic Chemistry", F. A. Cotton and G. Wilkinson, 4 Ed. p. 142 John Wiley & Sons (1980). In an article by D. L. Greene et al, *Journal of Inorganic and Nuclear Chemistry*, 35, 1471 (1973) there is a discussion of the spectral consequences of forming different kinds of complexes with dinitriles.

The recovery of values, e.g., nickel and boron from solid residue formed during the hydrocyanation of nitriles is disclosed in U.S. Pat. No. 4,082,811 issued on Apr. 4, 1978 and British Pat. No. 2,047,680 issued on Dec. 3, 1980.

A product stream from the hydrocyanation of 3-, 4-pentenenitriles to which the process of the present invention can be applied is disclosed in U.S. Pat. No. 3,773,809 issued on Nov. 20, 1973 as the stream comprising mono- and dinitriles after extraction of the product with a paraffin or cycloparaffin hydrocarbon.

SUMMARY OF THE INVENTION

This invention is directed to a process for recovering a triarylborane from solution in organic nitriles which comprises contacting said borane with a cyanide ion and a metal salt wherein said metal is selected from the class consisting of groups IIA, IB, IIB, VIIB and VIII in the presence of said nitrile and thereafter separating the reaction product from said nitrile.

A typical solution to which the process of the present invention is applied is obtained from the production of dinitriles by the addition of hydrogen cyanide to non-conjugated, unsaturated nitriles in the presence of a zero-valent nickelorganophosphorus ligand containing catalyst promoted with an arylborane wherein the product fluid from the addition is contacted with a paraffin or cycloparaffin to form a primary light hydrocarbon extract phase and a heavy dinitrile phase containing soluble catalyst and promoter. The present process recovers promoter which is soluble in the dinitrile phase.

DETAILED DESCRIPTION OF THE INVENTION

The present invention can be employed to improve promoter recovery in any process for the hydrocyanation of nitriles which employs a zero-valent nickel catalyst promoted with a triarylborane as described herein wherein eventually the product fluid is extracted with a paraffin or cycloparaffin.

The recovery of soluble promoter from the hydrocyanation of any non-conjugated, ethylenically unsaturated organic nitrile of from 4–20 carbon atoms is within the purview of this invention. Nitriles in which the promoter is dissolved and which can be present in the product fluid include monofunctional nitriles, e.g., 2-methyl-2-butenenitrile, 2-methyl-3-butenenitrile, 2-pentenenitrile, 3-pentenenitrile, 4-pentenenitrile, valeronitrile, butyronitrile, isobutyronitrile, propionitrile, acetonitrile, pentanonitrile, hexanonitrile, acrylonitrile, 2-butenenitrile, 2-hexenenitrile and 2-heptenenitrile, and difunctional nitriles, e.g., adiponitrile, methyl glutaronitrile, ethyl succinonitrile, methylene glutaronitrile, pimelonitrile, suberonitrile, azelonitrile and sebaconitrile. Of particular interest is the hydrocyanation of 3- and/or 4-pentenenitriles or mixtures thereof (3,4-PN's) to produce adiponitrile (ADN) because ADN is an intermediate used in the production of hexamethylenediamine which in turn is used to produce polyhexamethyleneadipamide, a commercial polyamide useful in forming fibers, films and molded articles.

The zero-valent nickel [Ni(O)] catalyst is prepared as described in U.S. Pat. No. 3,903,120 issued on Sept. 2, 1975, the disclosure of which patent is incorporated herein by this reference. Of particular interest is the preparation of a catalyst having the general formula $NiL_4$ where L is a neutral ligand such as a triarylphosphite of the formula $P(OAr)_3$ wherein Ar is an aryl group of up to 18 carbon atoms. Illustrative of the aryl groups are methoxyphenyl, tolyl xylyl and phenyl. Meta- and para-tolyl and mixtures thereof are the preferred aryl groups. Excess ligand can be employed.

The promoters which are used with the above-described catalyst, the soluble portion thereof which is recovered by the present process, are triarylboranes including those of the formula $BR_3$ wherein R is an aryl or substituted aryl group having 6–12 carbon atoms, e.g., phenyl, ortho-tolyl, para-tolyl, naphthyl, methoxyphenyl, biphenyl, chlorophenyl and bromophenyl. Illustrative of such boranes are triphenylborane, triorthotolylborane, triparatolylborane, triparachlorophenylborane, trixylylborane, tris-(3,4,5-trimethylphenyl)borane and trinaphthylborane. Triphenylborane (TPB) is preferred.

In order to separate dinitrile products from unreacted starting materials and catalysts which must be recycled for reasons of economy, the product fluid from the hydrocyanation after being treated to reduce the amount of pentenenitriles therein, e.g., by flash distillation is initially contacted with a paraffin or cycloparaffin, e.g., cyclohexane according to the process described in U.S. Pat. No. 3,773,809, the disclosure of which is incorporated herein by this reference. In the case of the hydrocyanation of 3-pentenenitrile (3PN) and/or 4-pentenenitrile (4PN) to produce adiponitrile (ADN) using $NiL_4$ wherein L is a neutral ligand tri(-mixed, meta- and para-)tolyl phosphite (TTP) as the catalyst and triphenylborane (TPB) as the promoter, a typical product fluid after flash distillation to remove a portion of the pentenenitriles present has the following average composition

| Component | Amount (% by weight) | |
|---|---|---|
| NiL$_4$ | 0.4–0.8 | (as Ni) |
| 3- and 4-PN | 10–20 | |
| TTP | 20–40 | |
| ADN + DN* | 40–60 | |
| TPB | 0.2–0.8 | |

*Dinitriles other than ADN such as 2-methyl-glutaronitrile and ethylsuccinonitrile This fluid product is exhaustively extracted with cyclohexane according to the process described in U.S. Pat. No. 3,773,809. The resulting phases are separated and the process of the present invention is applied to the heavy dinitrile phase.

The metals, which are employed as one of the reactants in the present process and with which the nitrile and boron moieties are coordinated to form a stable complex are the metals as set forth in the Periodic Table of the Elements as Group IIA—particularly Mg and Ca; Group IB—particularly Cu and Ag; Group IIB—particularly Zn and Cd; Group VIIB—particularly Mn; Group VIII—particularly Fe, Co, Ni, Ru, Rh and Pd. These metals are most conveniently introduced into the reaction medium as their salts of inorganic Bronsted acids, e.g., sulfate, chloride and nitrate or the hydrates of these salts. Specific examples include nickel chloride, nickel chloride hexahydrate, magnesium chloride hexahydrate, calcium chloride, copper (II) chloride dihydrate, silver nitrate, zinc nitrate, cadmium chloride hydrate, manganese (II) nitrate hexahydrate, ferrous sulfate heptahydrate, ferric chloride, cobaltous chloride hexahydrate, ruthenium (III) chloride and rhodium (III) chloride. Metals selected from the class consisting of Mg, Mn, Fe, Co, Ni, Cu, Zn and Cd are preferred. Divalent nickel, divalent iron and trivalent iron are especially preferred.

The cyanide can be introduced as hydrogen cyanide or as an alkali metal cyanide, e.g., sodium, potassium or lithium cyanide.

Generally, 0.5 mole of metal ion and 1.0 mole of cyanide is introduced into the reaction medium per mole of arylborane promoter contained therein. Up to a ten percent molar excess over the stoichiometric amount of the metal and cyanide can be employed to achieve substantially complete recovery of the borane but excesses above ten percent are not recommended.

The reaction can be conducted in the presence or absence of added solvent since the nitriles can act as a solvent or reaction medium. Generally, common organic solvents such as methylene chloride, chloroform, toluene, and chlorobenzene, which are inert to the reactants and product can be employed if a solvent is desired. Other solvents should be apparent to one skilled in the art.

The reaction, preferably with agitation, can be conducted over a wide range of temperature usually 0° to 100° C. and preferably 20° to 55° C.

In one preferred embodiment the cyanide is prereacted with the triarylborane before the introduction of the other reactants, although all the reactants can be contacted simultaneously. The metal salt should not be permitted to remain in contact with the source of cyanide for any appreciable time in the absence of the other reactants since these two compounds can react to form a metal cyanide and thereby decrease the yield of the desired complex.

It is possible to first prepare a soluble mononitrile complex, e.g., the complex formed from 3-pentenenitrile, the metal salt, an alkali metal cyanide and a triarylborane by the means discussed above. These complexes will generally be found to be soluble in the reaction medium. Should an insoluble dinitrile complex be desired, the addition of the dinitrile to the soluble complex will cause the precipitation of the dinitrile complex, except, of course, in such cases where the dinitrile complex is soluble itself.

The compounds produced by the process of the present invention are defined by the general formula

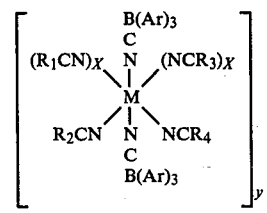

wherein X is 0 or 1, Y is a positive integer of 1–50, M is a metal selected from the class of metals of groups IIA, IB, IIB, VIIB and VIII; provided that when M is Pd, Ag, Cd, Pt, Au or Hg, X is 0; Ar is an aryl or substituted aryl group having 6–12 carbon atoms; $R_1$, $R_2$, $R_3$ and $R_4$ are the same or different and are groups selected from the class consisting of alkyl and substituted alkyl groups having 1–6 carbon atoms, alkenyl and substituted alkenyl groups having 2–6 carbon atoms, aryl groups having 6–10 carbon atoms and when adjacent nitrile groups are cojoined alkylene groups having 1–4 carbon atoms.

Of particular interest of the compounds produced by the present invention are those compounds defined by the general formula

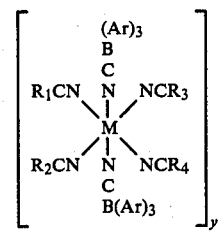

wherein y is a positive integer of 1–50; M is metal selected from the class consisting of $Ni^{++}$, $Fe^{++}$ and $Fe^{+++}$; Ar is selected from the group consisting of phenyl, orthotolyl, paratolyl and mixtures thereof; $R_1$–$R_4$ are the same or different and are groups selected from the class consisting of 1-methyl-1-propenyl, 1-methyl-2-propenyl, 1-butenyl, 2-butenyl, 3-butenyl, butyl, and when adjacent nitrile groups are cojoined ethylidene and ethylene.

The above described compounds can be monomeric, oligomeric or polymeric if the product stream is predominantly dinitriles and the compound consequently contains dinitrile ligands. In compounds with dinitrile ligands these ligands may have a free, unbound group; or they may be bridging, that is intermolecularly cojoined; or they may be chelating, that is intramolecularly cojoined. Generally, the number of monomer units in a polymeric compound will not exceed 50. The higher molecular weight compounds, e.g., $y=20$ or greater, tend to be solid while the compounds in solution tend to exhibit a lower molecular weight, e.g., $y=5$ or less.

The monomeric compounds made from mononitriles, and the bridge or chelated structures made from dinitriles show two nitrile absorption bands in their infrared spectra; one for the cyanoborate, and one for the alkylnitrile moiety. Eacch of these infrared resonances is shifted approximately 20–50 cm$^{-1}$ towards shorter wavelengths from its uncoordinated position. Nonchelated monomeric compounds made from dinitriles show three alkylnitrile absorptions; the third being the unco-ordinated part of the dinitrile.

The boron and metal values can be recovered from the complexes formed according to the process of the present invention by several methods including the method described in U.S. Pat. No. 4,082,811 issued on Apr. 4, 1978 particularly in column 5, line 58 through column 7, line 10.

The following examples are presented to illustrate but not to restrict the present invention. Parts and percentages are by weight unless otherwise noted.

EXAMPLE I

Approximately 380 parts of a process stream from the hydrocyanation of 3-,4-pentenenitrile having a composition within the general composition of the above-described process stream was exhaustively extracted with 600 part portions of cyclohexane at 20° C. according to the teachings of U.S. Pat. No. 3,773,809. The extracted liquid was filtered, under N$_2$, to remove deactivated catalyst solids, e.g., Ni[ADN]$_2$[NCB$\phi_3$]$_2$, Ni[CN]$_2$, etc. and 0.6 part of sodium cyanide was added to the filtrate. The mixture was stirred at 50° C. for ½ hour, under N$_2$, to dissolve the sodium cyanide and 3.6 parts of nickel (II) chloride hexahydrate were added. The mixture, gradually becoming turbid, was stirred under N$_2$ for an additional two hours at 50° C. and then allowed to stand overnight at room temperature. The solids which had formed were collected by centrifugation, reslurried and recentrifuged twice with toluene and twice with cyclohexane. The solids (4.8 parts) were repeatedly washed with water and recentrifuged until the supernatent liquid remained essentially colorless indicating the absence of nickel (II) chloride. The remaining material was dried at 50° C. overnight in a vacuum oven. The dried solids were analyzed by infrared spectrophotometry which showed the material to be about 60% Ni[ADN]$_2$[NCB$\phi_3$]$_2$ and 40% Ni[CN]$_2$.

EXAMPLE II

A hydrocyanation process stream was simulated by combining 100 parts of a 20% solution of triphenylborane in pentenenitriles (3-,4-PN) and 100 parts of adiponitrile. To this solution was added 4.07 parts of sodium cyanide. This combination was stirred for 5 minutes following which 9.69 parts of anhydrous nickel (II) chloride were added. The resulting mixture was stirred for five days. The slurry turned yellow-gray. Sodium chloride and unreacted nickel (II) chloride remained in the flask. To analyze the precipitate, the solids were removed by centrifugation, then reslurried and recentrifuged from, successively, acetonitrile, water (twice), acetonitrile, toluene, cyclohexane, and finally, dried. An infrared (ir) spectrum was taken of the pale blue solids (5 grams). The spectrum was identical to that of material isolated in Example I.

EXAMPLE III

A product fluid from the hydrocyanation of 3-,4-pentenenitrile was simulated by preparing a solution containing 653 parts adiponitrile, 155 parts pentenenitrile, and 25.5 parts of a 20.2% solution of triphenylborane in pentenenitriles (3-,4-PN) to which was added 1.41 parts of sodium cyanide and 3.92 parts of nickel (II) chloride hexahydrate. In 1–2 hours blue-green solids began to form. The mixture was stirred for four days at ambient temperature. The solids were recovered by centrifugation, twice reslurried in pentenenitriles and recentrifuged, reslurried in cyclohexane, filtered, reslurried in water, recentrifuged, and finally, reslurried with water and recovered by filtration. The solids were dried at 60° C. for three days in a vacuum oven. Infrared spectrophotometry showed the dried solids to be about 85% Ni[ADN]$_2$[NCB$\phi_3$]$_2$ and 15% Ni[CN]$_2$.

EXAMPLE IV

A product from the hydrocyanation of 3-,4-pentenenitriles after the addition of an alkali metal cyanide was simulated by combining 100 parts of adiponitrile, 4.0 parts of sodium cyanide and 102.6 parts of a 21.8% solution of triphenylborane in pentenenitriles. The resulting solution was thoroughly mixed by stirring for 20 minutes under a nitrogen blanket following which 11.12 parts of ferrous sulfate heptahydrate were added. The resulting mixture was stirred overnight at ambient temperature during which time a cream-colored slurry formed. The solids were recovered by centrifugation, successively reslurried with and recentrifuged from pentenenitrile, acetone and water (two times). After the second water wash the solids were recovered by filtration and then dried for three days in a vacuum oven at 60° C. An infrared spectrophotometric analysis showed the solids (19.93 parts) to be Fe[ADN]$_2$[NCB$\phi_3$]$_2$ representing a 50% recovery of the triphenylborane initially charged.

We claim:

1. A process for recovering a triarylborane in solution in organic nitriles which comprises reacting said borane with a cyanide ion and a metal salt wherein said metal is selected from the group consisting of groups IIA, IB, IIB, VIIB and VIII in the presence of said nitrile, and thereafter separating the boron containing reaction product from said nitrile.

2. The process of claim 1 wherein the aryl substituent of said borane is an aryl or substituted aryl group having 6–12 carbon atoms and the organic nitrile is selected from the group consisting of mononitriles, dinitriles and mixtures thereof having 2–8 carbon atoms.

3. The process of claim 1 wherein the metal of said metal salt is selected from the group consisting of Mg, Mn, Fe, Co, Ni, Cu, Zn and Cd.

4. The process of claim 1 wherein the source of cyanide ion is hydrogen cyanide, an alkali metal cyanide or mixtures thereof.

5. The process of claim 3 wherein the metal is introduced as a salt of an inorganic Bronsted acid.

6. The process of claims 1, 2, 3 or 4 wherein the organic nitriles comprise adiponitrile the triarylborane is triphenyl borane, and the metal is selected from the group consisting of Ni and Fe.

7. In a process for the production of dinitriles by the addition of hydrogen cyanide to non-conjugated, unsaturated nitriles in the presence of a zero-valent nickel-organophosphorus ligand containing catalyst promoted with an arylborane wherein the product fluid from said addition is contacted with a paraffin or cycloparaffin to form a primary light hydrocarbon extract phase and a heavy dinitrile phase containing soluble catalyst and promoter which phases are separated the improvement comprising recovering the arylborane by reacting said dinitrile phase with a cyanide ion and a metal salt wherein said metal is selected from the group consisting of groups IIA, IB, IIB, VIIB and VIII, separating the boron containing reaction product from said dinitrile phase.

8. The process of claim 7 wherein the metal of said metal salt is selected from the group consisting of Mg, Mn, Fe, Co, Ni, Cu, Zn and Cd.

9. The process of claim 7 wherein the source of cyanide ion is hydrogen cyanide, an alkali metal cyanide or mixtures thereof.

10. The process of claim 8 wherein the metal is introduced as a salt of an inorganic Bronsted acid.

11. The process of claims 7, 8, 9 or 10 wherein the dinitrile phase comprises adiponitrile, the triarylborane is triphenyl borane, and the metal is selected from the group consisting of Ni and Fe.

* * * * *